US011053178B2

(12) United States Patent
Pelati et al.

(10) Patent No.: US 11,053,178 B2
(45) Date of Patent: Jul. 6, 2021

(54) PARALLEL REACTOR SYSTEM FOR ETHYLBENZENE DEHYDROGENATION

(71) Applicant: FINA TECHNOLOGY, INC., Houston, TX (US)

(72) Inventors: Joseph E Pelati, Houston, TX (US); Jason Clark, Houston, TX (US)

(73) Assignee: FINA TECHNOLOGY, INC., Houston, TX (US)

( * ) Notice: Subject to any disclaimer, the term of this patent is extended or adjusted under 35 U.S.C. 154(b) by 0 days.

(21) Appl. No.: 15/838,569

(22) Filed: Dec. 12, 2017

(65) Prior Publication Data

US 2018/0170836 A1    Jun. 21, 2018

Related U.S. Application Data

(60) Provisional application No. 62/436,653, filed on Dec. 20, 2016.

(51) Int. Cl.
| | |
|---|---|
| *C07C 5/333* | (2006.01) |
| *C07C 15/46* | (2006.01) |
| *B01J 8/04* | (2006.01) |

(52) U.S. Cl.
CPC ............. *C07C 5/333* (2013.01); *B01J 8/0496* (2013.01); *C07C 5/3332* (2013.01); *C07C 15/46* (2013.01);

(Continued)

(58) Field of Classification Search
CPC ........... C07C 5/333; C07C 5/327; C07C 5/32; C07C 15/46
See application file for complete search history.

(56) References Cited

U.S. PATENT DOCUMENTS

| 4,628,136 A | * | 12/1986 | Sardina | ..................... C07C 7/04 585/441 |
| 6,380,449 B1 | * | 4/2002 | Butler | .................... B01J 8/0292 422/205 |

(Continued)

FOREIGN PATENT DOCUMENTS

| CN | 103664497 A | 3/2014 | |
| EP | 3000800 A1 | * 3/2016 | ............... C07C 5/52 |
| EP | 3000800 A1 | 3/2016 | |

OTHER PUBLICATIONS

Foreign communication from a counterpart application—International Search Report and Written Opinion, PCT/US2017/065709, dated Mar. 5, 2018, 13 pages.

*Primary Examiner* — Youngsul Jeong
(74) *Attorney, Agent, or Firm* — Albert Shung

(57) ABSTRACT

A multi-stage dehydrogenation process including contacting, in a first stage, a feed stream comprising a hydrocarbon and steam with a dehydrogenation catalyst under dehydrogenation conditions to yield a first stage effluent, heating the first stage effluent, and contacting, in a second stage, the heated first stage effluent with a dehydrogenation catalyst under dehydrogenation conditions to yield a second stage effluent comprising a dehydrogenation product, wherein the first stage includes a first reactor and a second reactor arranged in parallel, and wherein the second stage includes a third reactor connected in series with the first reactor and the second reactor. A multi-stage dehydrogenation system for carrying out dehydrogenation is also provided.

18 Claims, 3 Drawing Sheets

(52) U.S. Cl.
CPC .... *B01J 8/0492* (2013.01); *B01J 2208/00061* (2013.01); *B01J 2208/00168* (2013.01); *B01J 2208/00539* (2013.01); *B01J 2208/00893* (2013.01); *B01J 2219/0004* (2013.01); *B01J 2219/00038* (2013.01); *C07C 2523/04* (2013.01); *C07C 2523/745* (2013.01); *C07C 2523/78* (2013.01)

(56) References Cited

U.S. PATENT DOCUMENTS

| | | | |
|---|---|---|---|
| 2009/0264692 A1 | 10/2009 | Welch et al. | |
| 2009/0318741 A1 | 12/2009 | Newman | |
| 2016/0288079 A1* | 10/2016 | Oleksy | B01J 19/0013 |

* cited by examiner

PARALLEL REACTOR SYSTEM FOR ETHYLBENZENE DEHYDROGENATION

CROSS-REFERENCE TO RELATED APPLICATIONS

The present application claims priority under 35 U.S.C. § 119(e) to U.S. Provisional Patent Application No. 62/436,653 filed on Dec. 20, 2016, and entitled "Parallel Reactor System for Ethylbenzene Dehydrogenation," the disclosure of which is hereby incorporated by reference in its entirety.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD

The disclosed systems and processes relate to dehydrogenation reactions, for example, the dehydrogenation of ethylbenzene to styrene monomer. More particularly, the disclosed systems and processes relate to multi-stage dehydrogenation. Still more particularly, the disclosed systems and processes relate to multi-stage dehydrogenation comprising a first stage comprising two dehydrogenation reactors arranged in parallel, in series with a second stage comprising a third dehydrogenation reactor.

BACKGROUND

Styrene, a raw material for major polymer products such as polystyrene, acrylonitrile butadiene styrene, styrene butadiene rubber, and others, is consumed in great quantities annually, being one of the representative general-purpose monomer products. Conventional styrene manufacturing plants utilize a reaction system comprising two or three adiabatic reactors connected in series, in conjunction with a number of furnaces and heat exchangers. Styrene can be prepared by dehydrogenating ethylbenzene in the presence of overheated water vapor, i.e. steam, on a dehydrogenation catalyst bed in a reactor. In view of the commercial importance of styrene production, there exists an ongoing need for improved systems and processes for effecting dehydrogenation reactions, such as the dehydrogenation of ethylbenzene to produce styrene. Desirably, such improved systems and processes may enable a reduction in reactor pressure, an increase in selectivity, desirable conversion, and/or a reduction in the energy input required per pound of desired dehydrogenation product, as will be described in more detail herein.

SUMMARY

Herein disclosed is a multi-stage dehydrogenation process comprising: contacting, in a first stage, a feed stream comprising a hydrocarbon and steam with a dehydrogenation catalyst under dehydrogenation conditions to yield a first stage effluent; heating the first stage effluent; and contacting, in a second stage, the heated first stage effluent with a dehydrogenation catalyst under dehydrogenation conditions to yield a second stage effluent comprising a dehydrogenation product, wherein the first stage includes a first reactor and a second reactor arranged in parallel, and wherein the second stage includes a third reactor connected in series with the first reactor and the second reactor. In embodiments, contacting the feed stream in the first stage comprises: contacting a first portion of the feed stream with the dehydrogenation catalyst in the first reactor to yield a first reactor effluent; and contacting a second portion of the feed stream with the dehydrogenation catalyst in the second reactor to yield a second reactor effluent. In embodiments, the method further comprises combining the first reactor effluent and the second reactor effluent to form the first stage effluent prior to the step of heating. In embodiments, the method further comprises heat exchanging the feed stream with the second stage effluent, thereby condensing a portion of the second stage effluent; compressing the second stage effluent after the step of heat exchanging; and separating the dehydrogenation product from the second stage effluent. In embodiments, a total differential pressure of the multi-stage dehydrogenation process is less than a total differential pressure of an otherwise similar process in which the first reactor, the second reactor, and the third reactor are connected in series, wherein the total differential pressure is measured between an inlet of the first reactor and an outlet of the third reactor. In embodiments, an overall selectivity of the multi-stage dehydrogenation process is greater than an overall selectivity of an otherwise similar process in which the first reactor, the second reactor, and the third reactor are connected in series, wherein the overall selectivity is defined as: [moles of desired product (e.g., dehydrogenation product) produced in the first reactor, the second reactor, and the third reactor]/[total moles of dehydrogenation feed species (e.g., hydrocarbon) converted in the first reactor, the second reactor, and the third reactor]. In embodiments, a total energy input of the multi-stage dehydrogenation process is less than a total energy input of an otherwise similar process in which the first reactor, the second reactor, and the third reactor are connected in series. In embodiments, the hydrocarbon is ethylbenzene, and the dehydrogenation product comprises styrene. In embodiments, each of the first reactor, the second reactor, and the third reactor is an adiabatic reactor. In embodiments, heating the first stage effluent uses a heat exchanger.

Also disclosed herein is a multi-stage dehydrogenation system comprising: a feed stream comprising a hydrocarbon and steam; a first stage having a first reactor and a second reactor arranged in parallel, wherein the first reactor contains a dehydrogenation catalyst and has a first reactor inlet which receives a portion of the feed stream, wherein the second reactor contains a dehydration catalyst and has a second reactor inlet which receives a remaining portion of the feed stream, and wherein the first stage is effective to convert at least a portion of the hydrocarbon to a dehydrogenation product by contacting the hydrocarbon with the dehydrogenation catalyst in the first and second reactors under dehydrogenation conditions; an inter-stage heater fluidly connected to a first reactor outlet of the first reactor and receiving a first reactor effluent and fluidly connected to a second reactor outlet of the second reactor and receiving a second reactor effluent; a second stage having a third reactor, wherein the third reactor contains a dehydrogenation catalyst and has a third reactor inlet in fluid communication with the heater, and wherein the second stage is effective to convert unreacted hydrocarbon received from the inter-stage heater to the dehydrogenation product by contacting the unreacted hydrocarbon with the dehydrogenation catalyst in the third reactor under dehydrogenation conditions to provide a second stage effluent comprising an effluent from the third reactor. In embodiments, the first reactor effluent and the second reactor effluent are combined to form a first stage effluent which feeds to the inter-stage heater. In embodiments, the inter-stage heater is a heat exchanger which uses steam as a heating fluid. In embodiments, the system further comprises a first heat exchanger which exchanges a first heat between the second stage effluent and the feed stream; and a second heat exchanger which exchanges a second heat between the second stage effluent and the feed stream. In embodiments, the system further comprises a compressor downstream of the first heat exchanger and the second heat exchanger and configured to compress the second stage effluent; and a separation system downstream of the compressor and configured to separate a dehydrogenation product from the second stage effluent. In embodiments, a total differential pressure of the multi-stage dehydrogenation process is less than a total differential pressure of an otherwise similar system in which the first reactor, the second reactor, and the third reactor are connected in series, wherein the total differential pressure is measured between the first reactor inlet and an outlet of the third reactor. In embodiments, an overall selectivity of the multi-stage dehydrogenation process is greater than an overall selectivity of an otherwise similar system in which the first reactor, the second reactor, and the third reactor are connected in series, wherein the overall selectivity is defined as: [moles of desired product (e.g., dehydrogenation product) produced in the first reactor, the second reactor, and the third reactor]/[total moles of dehydrogenation feed species (e.g., hydrocarbon) converted in the first reactor, the second reactor, and the third reactor]. In embodiments, a total energy input of the multi-stage dehydrogenation process is less than a total energy input of an otherwise similar system in which the first reactor, the second reactor, and the third reactor are connected in series. In embodiments, the hydrocarbon is ethylbenzene, and the dehydrogenation product comprises styrene. In embodiments, each of the first reactor, the second reactor, and the third reactor is an adiabatic reactor.

Also disclosed herein is a multi-stage dehydrogenation process comprising: combining steam and ethylbenzene to form a feed stream; heating the feed stream to yield a heated feed stream; splitting the heated feed stream into a first portion and a second portion; feeding the first portion of the feed stream to a first reactor containing a dehydrogenation catalyst, wherein ethylbenzene is converted to styrene; feeding the second portion of the feed stream to a second reactor containing a dehydrogenation catalyst, wherein ethylbenzene is converted to styrene; recovering from the first reactor a first effluent comprising unreacted ethylbenzene and styrene; recovering from the second reactor a second effluent comprising unreacted ethylbenzene and styrene; combining the first effluent and the second effluent into a combined effluent; heating the combined effluent to yield a heated combined effluent; feeding the heated combined effluent to a third reactor containing a dehydrogenation catalyst, wherein at least a portion of the unreacted ethylbenzene present in the heated combined effluent is converted to styrene; and recovering from the third reactor a third effluent comprising unreacted ethylbenzene and styrene.

BRIEF DESCRIPTION OF THE DRAWINGS

The detailed description will reference the drawings briefly described below, wherein like reference numerals represent like parts.

DETAILED DESCRIPTION

Figure 1:
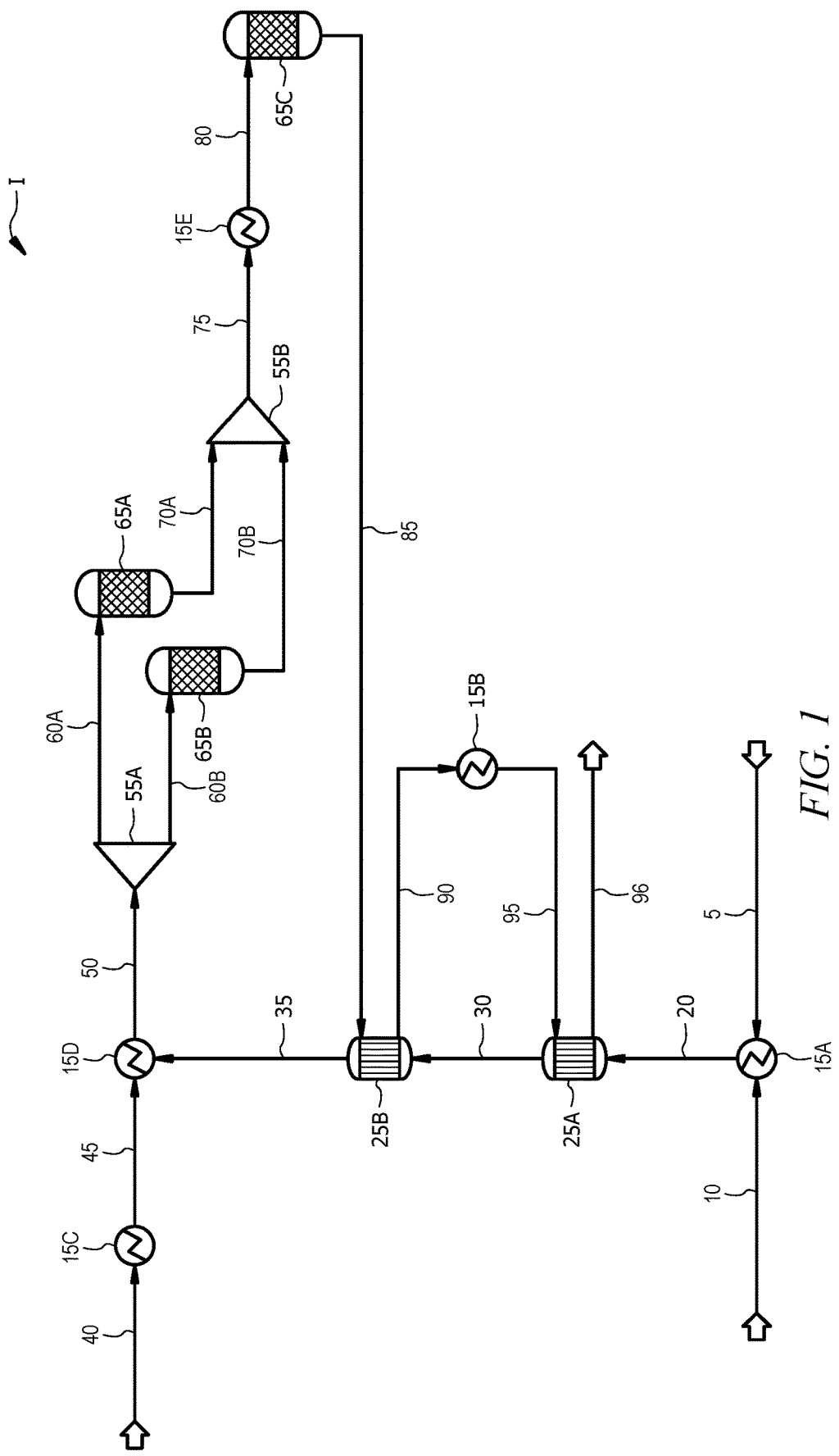
FIG. 1 is a process flow diagram of a multi-stage dehydrogenation system according to an embodiment of this disclosure.

Conventional processes for dehydrogenation (e.g., dehydrogenation of ethylbenzene) generally involve steam dilution, reduced pressure operation, and adiabatic reactors. For endothermic reactions, reheaters are located between the adiabatic reactors. The dehydrogenation reaction may be favored at low pressure, so the reactors are typically operated at reduced pressure (i.e., vacuum conditions) by installing a compressor (e.g., a vacuum compressor) on the effluent line. Conventional three-bed reactor systems are arranged in series, and are common retrofit options for increasing plant capacity. For example, dehydrogenation of ethylbenzene is endothermic, and involves steam dilution and serial, adiabatic reactors, with reheaters located between the reactors.

As noted hereinabove, conventional dehydrogenation employs three dehydrogenation reactors arranged in series. It has been surprisingly found that arranging the first two reactors of a multi-stage dehydrogenation application in parallel, and subsequently combining the product streams thereof to feed a common third reactor may enable a lowering of the overall reactor pressure, a decrease in energy needs, and/or an increase in product selectivity, while maintaining desirable conversion. Although at times described hereinbelow with reference to dehydrogenation of ethylbenzene to produce styrene monomer, it will be apparent to those of skill in the art that the herein disclosed system and process may be suitable for a variety of dehydrogenation reactions.

It should be understood at the outset that although illustrative implementations of one or more aspects are illustrated below, the disclosed assemblies, systems, and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents. While values for dimensions of various elements are disclosed, the drawings may not be to scale.

Disclosed herein are a system and process for multi-stage dehydrogenation. The system and process utilize three reactors, the first two of which are arranged in parallel and feed serially into a common third reactor, as described in more detail hereinbelow. As noted hereinabove, such parallel arrangement of the first two reactors may enable lower overall reactor pressure, a decrease in energy requirements, and/or an increase in selectivity.

Herein disclosed is a system for multi-stage dehydrogenation. The system comprises a first stage comprising a first dehydrogenation reactor and a second dehydrogenation reactor arranged in parallel; a second stage arranged in series with the first stage and comprising a third dehydrogenation reactor; and an inter-stage heater fluidly connected to an outlet of each of the first dehydrogenation reactor and the second dehydrogenation reactor and configured to raise the temperature of reactor effluent therefrom and introduce an elevated temperature reactor effluent into the third dehydrogenation reactor. The system may further comprise one or more heaters in addition to the inter-stage heater, one or more heat exchangers, one or more flow splitters or mixers, and various downstream processing equipment, such as compressors and separators configured to separate the multi-stage dehydrogenation product from a reactor effluent extracted from the third reactor. For example, in embodiments such as that described hereinbelow with reference to FIG. 1, a multi-stage dehydrogenation system according to this disclosure may comprise a first heat exchanger configured to exchange a first heat between a second stage effluent and the feed stream, and may further comprise a second heat exchanger configured to exchange a second heat between the second stage effluent and the feed stream. In some embodiments, a multi-stage system according to this disclosure further comprises a compressor located downstream of the third reactor, the first heat exchanger and/or the second heat exchanger, and configured to compress a second stage effluent, and may also, in embodiments, comprise a separation system located downstream of the compressor and configured to separate a dehydrogenation product from the second stage effluent. Each of the components of a system of this disclosure mentioned hereinabove will now be described in more detail with reference to the embodiment of FIG. 1.

FIG. 1 is a process flow diagram of a multi-stage dehydrogenation system I according to an embodiment of this disclosure. Multi-stage dehydrogenation system I comprises first and second reactor stages in series, each stage effective to convert at least a portion of a hydrocarbon in a feed stream comprising the hydrocarbon and steam into a dehydrogenation product by contacting the hydrocarbon with a dehydrogenation catalyst under dehydrogenation conditions. The first reactor stage of multi-stage dehydrogenation system I comprises a first dehydrogenation reactor 65A and a second dehydrogenation reactor 65B arranged in parallel, and the second reactor stage of multi-stage dehydrogenation system I comprises third dehydrogenation reactor 65C. Multi-stage dehydrogenation system I further comprises first heater 15A, second heater 15B, third heater 15C, fourth heater 15D, inter-stage heater 15E (also referred to herein as 'fifth heater 15E'), flow splitter 55A, mixer 55B, first heat exchanger 25A, and second heat exchanger 25B. Each of the components of multi-stage dehydrogenation system I will be described in more detail hereinbelow.

First heater 15A is configured to produce a first heater effluent in first heater effluent line 20 by combining a hydrocarbon feed introduced thereto via hydrocarbon feed inlet line 10 and vaporizing steam introduced thereto via vaporizing steam feed inlet line 5. First heater 15A is operable to vaporize the hydrocarbon feed introduced thereto, and thus is also referred to herein at times as 'vaporizer steam mixing unit 15A'. First heater 15A is fluidly connected with first heat exchanger 25A via first heater effluent line 20. First heat exchanger 25A is configured for the exchange of heat between the first heater effluent in first heater effluent line 20 and the second heater effluent in second heater effluent line 95. As first heat exchanger 25A is operable to vaporize hydrocarbon introduced thereto via first heater effluent line 20, first heat exchanger 25A is sometimes referred to herein as 'reactor feed vaporizer 25A'. First heat exchanger effluent line 96 is configured for the removal of effluent comprising dehydrogenation product from first heat exchanger 25A, and first heat exchanger effluent line 30 is configured for the removal of effluent comprising reactor feed from first heat exchanger 25A.

First heat exchanger 25A is fluidly connected with second heat exchanger 25B via first heat exchanger effluent line 30, and is configured for the exchange of heat between the first heat exchanger effluent comprising reactor feed in first heat exchanger effluent line 30 and the third reactor effluent extracted from the third dehydrogenation reactor 65C via third reactor effluent line 85. Second heat exchanger effluent line 90 is configured for the removal of effluent comprising dehydrogenation product from second heat exchanger 25B, and second heat exchanger effluent line 35 is configured for the removal of effluent comprising reactor feed from second heat exchanger 25B. As second heat exchanger 25B is configured to transfer heat from the effluent of the third dehydrogenation extracted from third dehydrogenation reactor 65C via third reactor effluent line 85 and the first heat exchanger effluent comprising reactor feed in first heat exchanger effluent line 30, second heat exchanger 25B is also referred to herein as 'reactor feed/effluent exchanger 25B'. A second heater 15B may be positioned to receive and heat second heat exchanger effluent comprising dehydrogenation product introduced thereto via second heat exchanger effluent line 90, and provide a second heater effluent extracted therefrom via second heater effluent line 95. As second heater 15B may be operable to generate high pressure (HP) steam, second heater 15B may be referred to herein as 'HP steam generator 15B'.

Third heater 15C is configured to produce a third heater effluent from dilution steam introduced via dilution steam feed line 40. As third heater 15C may be operable to superheat the dilution steam introduced thereto via dilution steam feed line 40, third heater 15C may be referred to herein as 'first steam superheater 15C'. Third heater 15C is fluidly connected with fourth heater 15D via third heater effluent line 45. Fourth heater 15D is configured to produce a fourth heater effluent from dilution steam introduced thereto via third heater effluent line 45 and hydrocarbon feed introduced thereto via second heat exchanger effluent line 35. As fourth heater 15D provides dilution steam mixing (i.e., the contents of line 35 and line 45 are combined and discharged via effluent line 50), fourth heater 15D may be referred to herein as 'dilution steam mixing unit 15D'. Fourth heater effluent line 50 (also referred to herein as 'first stage feed line 50') fluidly connects fourth heater 15D and flow splitter 55A, and is configured for the extraction of first stage reactor feed from fourth heater 15D and introduction thereto into flow splitter 55A.

Flow splitter 55A is configured to split the first stage reactor feed introduced thereto via fourth heater effluent flow line 50 for introduction into parallel dehydrogenation reactors 65A and 65B. Flow splitter 55A is fluidly connected with first dehydrogenation reactor 65A via first dehydrogenation reactor feed line 60A, and with second dehydrogenation reactor 65B via second dehydrogenation reactor feed line 60B.

First dehydrogenation reactor 65A contains a dehydrogenation catalyst, and comprises a first reactor inlet which receives a portion, via first dehydrogenation reactor feed line 60A, of the first stage feed comprising a hydrocarbon and steam in first stage feed line 50; second dehydrogenation reactor 65B also contains a dehydration catalyst, and comprises a second reactor inlet which receives a remaining portion, via second dehydrogenation reactor feed line 60B, of the first stage feed comprising a hydrocarbon and steam in first stage feed line 50.

First dehydrogenation reactor 65A is fluidly connected via a first reactor outlet with mixer 55B; second dehydrogenation reactor 65B is fluidly connected via a second reactor outlet with mixer 55B. Mixer 55B is configured to combine the first dehydrogenation reactor effluent extracted from first dehydrogenation reactor 65A via first reactor effluent line 70A and the second dehydrogenation reactor effluent extracted from second dehydrogenation reactor 65B via second reactor effluent line 70B, to provide a combined first stage reactor effluent. Mixer 55B is fluidly connected via combined first stage effluent line 75 with fifth heater 15E (also referred to herein as 'inter-stage heater 15E' or 'third reactor reheater 15E'). Fifth heater 15E is configured to increase the temperature of the first stage effluent introduced thereto via first stage effluent line 75 prior to introduction into the second stage comprising third dehydrogenation reactor 65C. Third reactor feed line 80 (also referred to herein as 'second stage feed line 80') fluidly connects fifth heater 15E with third dehydrogenation reactor 65C.

As noted hereinabove, a third reactor effluent line 85 comprising dehydrogenation product fluidly connects third dehydrogenation reactor 65C with second heat exchanger 25B. Also as noted hereinabove (and not indicated in FIG. 1), multi-stage dehydrogenation system I may further comprise downstream processing apparatus as known to those of ordinary skill in the art. By way of non-limiting example, a multi-stage dehydrogenation system according to this disclosure may further comprise a compressor configured for the introduction thereto of the third reactor effluent (e.g., via first heat exchanger effluent line 96), and separations units designed to separate the dehydrogenation product from water and various by-products of the reaction.

Figure 2:
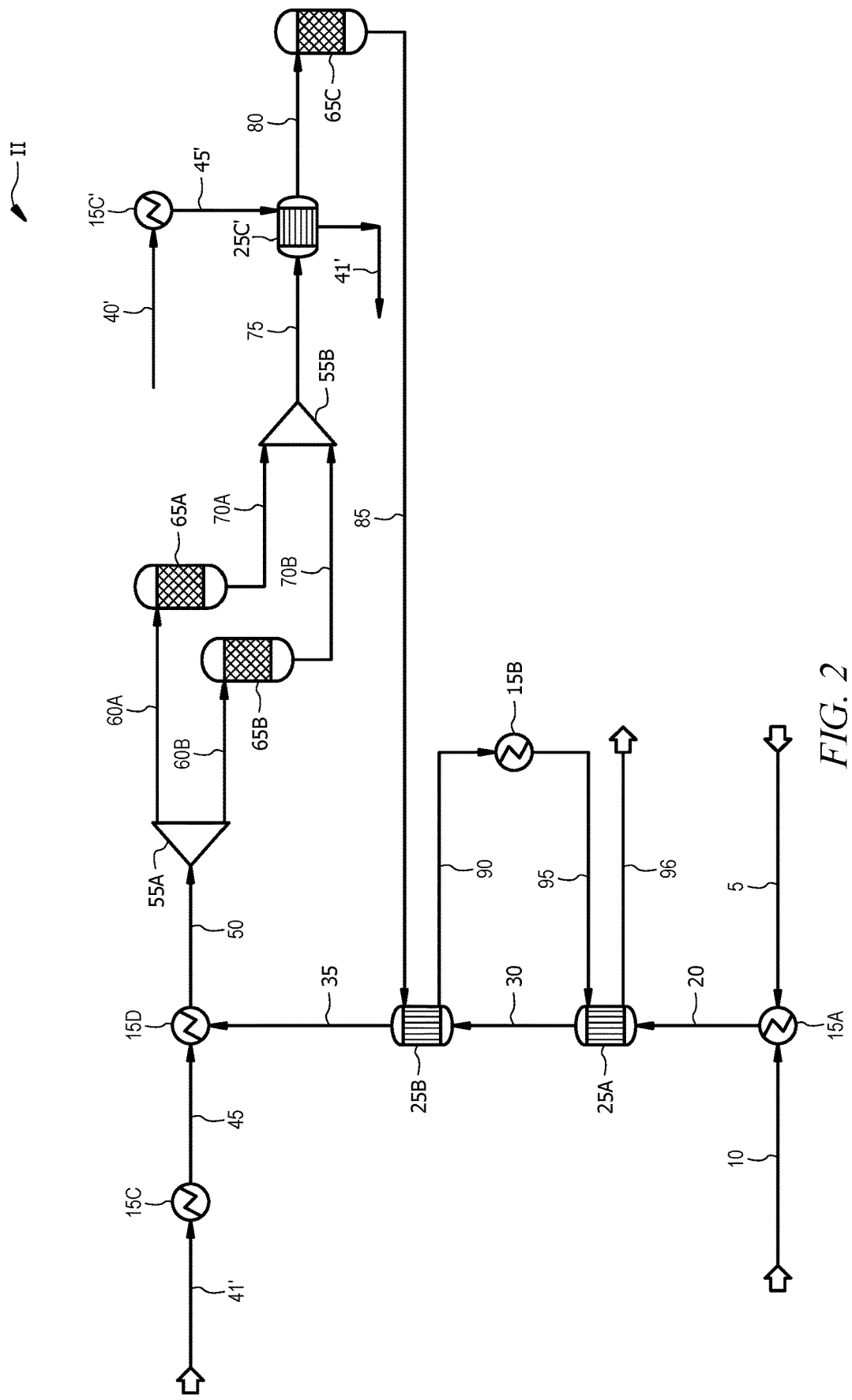
FIG. 2 is a process flow diagram of a multi-stage dehydrogenation system according to another embodiment of this disclosure.

A multi-stage dehydrogenation system II according to another embodiment of this disclosure is illustrated in the process flow diagram of FIG. 2. In this embodiment, dilution steam feed line 40' is configured for the introduction of dilution steam feed into third heater 15C' (also referred to herein as 'first steam superheater 15C"), which is, in this embodiment, fluidly connected with third heat exchanger 25C' via third heater effluent line 45'. A line 41' may fluidly connect third heat exchanger 25C' with dilution steam mixing unit 15D, via third heater 15C and third heater effluent line 45. Third heater 15C will provide additional reheat prior to mixing with the hydrocarbon stream to enter the first set of reactors. In this embodiment, the inter-stage heater comprises heat exchanger 25C'. This embodiment may enable a further energy advantage over the embodiment of FIG. 1, relative to the conventional embodiment of FIG. 3 described further hereinbelow, due to the enhanced heat recovery and slightly lower total energy input.

Dehydrogenation reactors 65A, 65B, and 65C may be any dehydrogenation reactors known to those of skill in the art. In embodiments, dehydrogenation reactors 65A, 65B, and 65C are adiabatic reactors. Dehydrogenation reactors 65A, 65B, and 65C contain therein dehydrogenation catalyst suitable to catalyze the dehydrogenation of hydrocarbon in the hydrocarbon feed to dehydrogenation product. In embodiments, the dehydrogenation catalyst is a catalyst operable to dehydrogenate ethylbenzene in a hydrocarbon feed to produce a dehydrogenation product comprising styrene. One of skill in the art will find apparent the selection of a suitable dehydrogenation catalyst based on the given reactor conditions. In embodiments, the dehydrogenation catalyst comprises iron (III) oxide, promoted by potassium oxide or potassium carbonate, rare earth oxides and/or other inorganic performance promoters. In embodiments, the dehydrogenation catalyst comprises a heterogeneous catalyst system suited to operate with steam dilution, reduced pressure and high temperature to overcome the equilibrium constraints and the endothermic reaction.

Heaters 15A, 15B, 15C, 15C', 15D, and 15E may be any heaters known to those of skill in the art. In embodiments, one or more of heaters 15A, 15B, 15C, 15C', 15D, and 15E are selected from fired tube heaters or furnaces. In embodiments, one or more of heaters 15A, 15B, 15C, 15C', 15D, and 15E are selected from heat exchangers. In embodiments, one or more of heaters 15A, 15B, 15C, 15C', 15D, and 15E are selected from heat exchangers which use steam as a heating fluid. In embodiments, second heater 15B is a HP steam generator. In embodiments, third heater 15C, third heater 15C', or both are steam superheaters. In embodiments, inter-stage heater 15E comprises a standard furnace reheater. In embodiments, inter-stage heater 15E comprises a heat exchanger.

Heat Exchangers 25A, 25B and 25C' may be any heat exchangers known to those of skill in the art to be suitable for exchanging heat between a process stream and a heat exchange fluid. In embodiments, the heat exchange fluid comprises steam. In embodiments, the heat exchange fluid comprises another process stream (e.g., third reactor effluent in third reactor effluent line 85, second heat exchanger effluent in second heat exchanger effluent line 90, or second heater effluent in second heater effluent line 95). In embodiments, heat exchangers 25A, 25B, and/or 25C' are selected from shell and tube heat exchangers.

Figure 3:
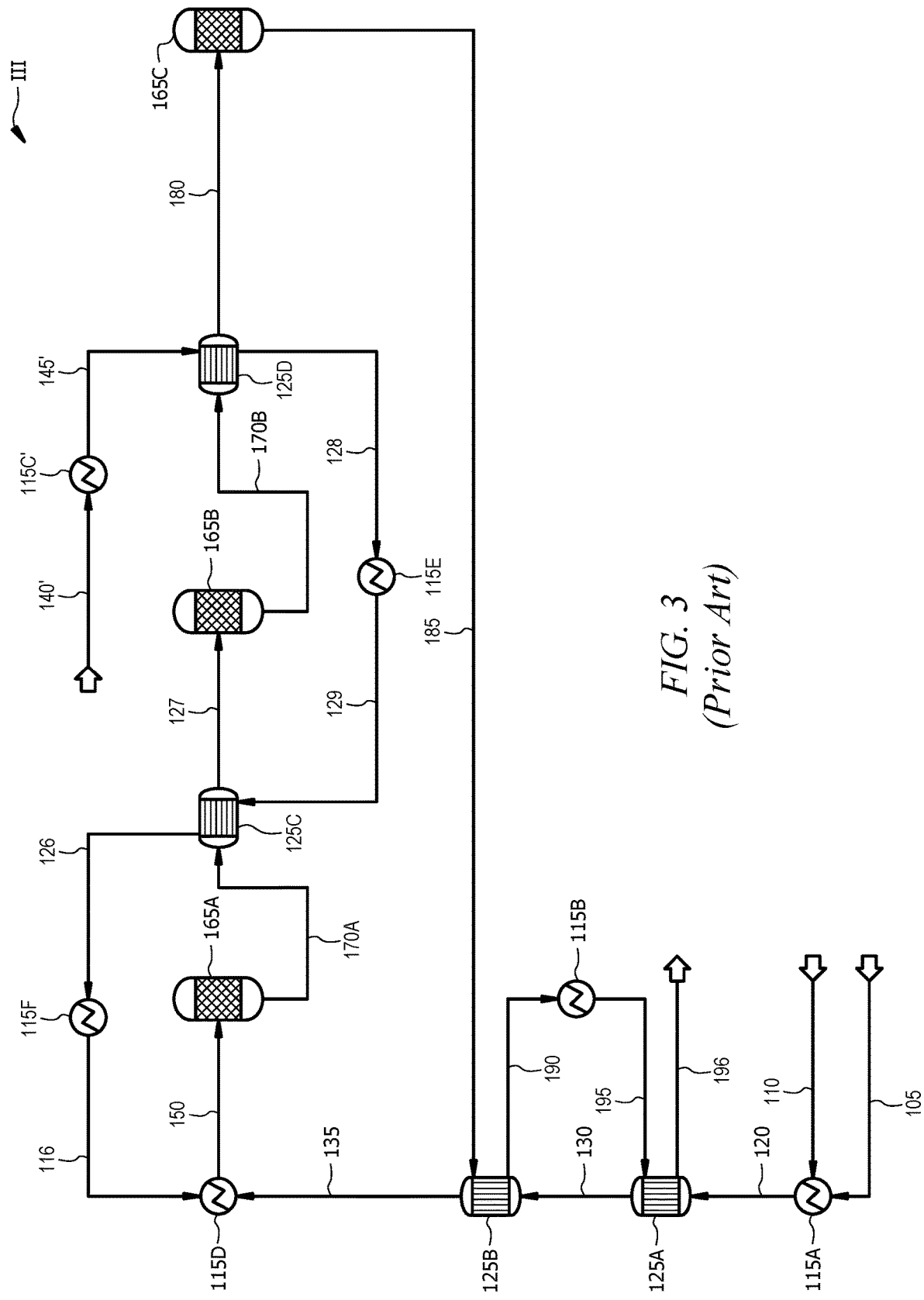
FIG. 3 is a process flow diagram of a prior art dehydrogenation system.

By way of comparison, a conventional dehydrogenation system III according to the prior art is illustrated in FIG. 3, and will be referred to for comparison in the Examples hereinbelow. Numbering in FIG. 3 generally corresponds to that of FIGS. 1 and 2, except as noted hereinbelow (specifically with regard to fifth heater 115E), with the components on FIG. 3 being increased by 100, e.g., component 105 in FIG. 3 corresponds with component 5 in FIGS. 1 and 2.

In conventional dehydrogenation system III, first dehydrogenation reactor 165A, second dehydrogenation reactor 165B, and third dehydrogenation reactor 165C are connected in series. In this configuration, fourth heater effluent in fourth heater effluent line 150 is not introduced into a flow splitter, but is, rather, all introduced into first dehydrogenation reactor 165A. The first dehydrogenation reactor effluent is introduced via first reactor effluent line 170A into the second dehydrogenation reactor 165B via a third heat exchanger 125C and third heat exchanger effluent line 127. Third heat exchanger 125C is configured to exchange heat between first reactor effluent in first reactor effluent line 170A and steam in the fifth heater effluent in fifth heater steam effluent line 129. As third heat exchanger 125C serves to reheat reactants prior to second dehydrogenation reactor 165B, third heat exchanger 125C may be referred to herein as 'reactor 1/reactor 2 reheater 125C'. The second dehydrogenation reactor effluent is introduced via second reactor effluent line 170B into third dehydrogenation reactor 165C via a fourth heat exchanger 125D and third reactor feed line 180. As fourth heat exchanger 125D is operable to provide a heated feed to third dehydrogenation reactor 165C, fourth heat exchanger 125D is also referred to herein as 'reactor 2/reactor 3 reheater 125D'.

Dilution steam feed inlet line 140' is configured to introduce dilution steam into third heater 115C' which is configured to heat the dilution steam. As third heater 115C' may be operable to superheat the dilution steam introduced thereto, third heater 115C' may be referred to herein as 'first steam superheater 115C"'. Third heater effluent line 145' fluidly connects third heater 115C' with fourth heat exchanger 125D, which is configured for the transfer of heat from the steam in third heater effluent line 145' to the second reactor effluent introduced into fourth heat exchanger 125D via second reactor effluent line 170B, thus heating the second reactor effluent for introduction into third dehydrogenation reactor 165C via third reactor feed line 180, and providing a cooled steam extracted from fourth heat exchanger 125D via fourth heat exchanger steam effluent line 128. Fourth heat exchanger steam effluent line 128 fluidly connects fourth heat exchanger 125D with fifth heater 115E (which is not an inter-stage heater in this conventional case), which is configured to heat the cooled steam introduced thereto. As fifth heater 115E may operate to provide superheated steam, fifth heater 115E may be referred to herein as 'second steam superheater 115E'. A fifth heater effluent line 129 fluidly connects fifth heater 115E with third heat exchanger 125C which, as noted hereinabove, is configured to exchange heat between first reactor effluent in first reactor effluent line 170A and steam in the fifth heater effluent in fifth heater steam effluent line 129. Third heat exchanger steam effluent line 126 fluidly connects third heat exchanger 125C with sixth heater 115F, which is configured to heat the cooled steam introduced thereto via third heat exchanger steam effluent line 126, prior to combination thereof in fourth heater 155D with the second heat exchanger effluent comprising reactor feed in second heat exchanger effluent line 135. As sixth heater 115F may be operable to superheat the steam introduced thereto, sixth heater 115F may be referred to herein as 'third steam superheater 115F'.

Components 105 (vaporizing steam feed inlet line), 110 (hydrocarbon feed inlet line), 115A ('first heater' or 'vaporizer steam mixing unit'), 115B ('second heater' or 'HP steam generator'), 120 (first heater effluent line), 125A ('first heat exchanger' or 'reactor feed vaporizer'), 125B ('second heat exchanger' or 'reactor feed/effluent exchanger'), 130 (first heat exchanger effluent line comprising reactor feed), 190 (second heat exchanger effluent line comprising dehydrogenation products), 195 (second heater effluent line comprising dehydrogenation product), and 196 (first heat exchanger effluent line comprising dehydrogenation product) of FIG. 3 are as described with reference to components 5, 10, 15A, 15B, 20, 25A, 25B, 30, 90, 95, and 96 of FIGS. 1 and 2.

Also disclosed herein is a process for multi-stage dehydrogenation. The multi-stage process comprises contacting, in a first stage, a feed stream comprising a hydrocarbon and steam with a dehydrogenation catalyst under dehydrogenation conditions to yield a first stage effluent; heating the first stage effluent; and contacting, in a second stage, the heated first stage effluent with a dehydrogenation catalyst under dehydrogenation conditions to yield a second stage effluent comprising a dehydrogenation product, wherein the first stage includes a first reactor and a second reactor arranged in parallel, and wherein the second stage includes a third reactor connected in series with the first reactor and the second reactor. In embodiments, the hydrocarbon is ethylbenzene, and the dehydrogenation product comprises styrene. In embodiments, each of the first reactor, the second reactor, and the third reactor is operated adiabatically.

A more detailed description of the multi-stage process, according to an embodiment of this disclosure, will now be made with reference to FIG. 1.

Vaporizing steam feed in vaporizing steam feed inlet line 5 and hydrocarbon feed in hydrocarbon feed inlet line 10 are combined in first heater 15A, wherein the hydrocarbon is vaporized, to provide a first heater effluent comprising a vaporized hydrocarbon feed which is extracted from first heater 20 via first heater effluent line 20. Via passage through first heat exchanger 25A and second heat exchanger 25B, heat is exchanged between the vaporized hydrocarbon feed and a third reactor effluent (i.e., the product stream) in third reactor effluent line 85. In first heat exchanger 25A, heat is exchanged between the vaporized hydrocarbon feed in first heater effluent line 20 and the second heater effluent comprising dehydrogenation product in second heater effluent line 95. Dehydrogenation product is extracted from first heat exchanger 25A via first heat exchanger effluent line 96, and first heat exchanger effluent comprising reactor feed is extracted from first heat exchanger 25A via first heat exchanger effluent line 30. Further heat exchange of the hydrocarbon feed extracted from first heat exchanger 25A via first heat exchanger effluent line 30 is provided by introduction thereof into second heat exchanger 25B and heat exchange with the product stream extracted from third dehydrogenation reactor 65C via third reactor effluent line 85. Dehydrogenation product is extracted from second heat exchanger 25B via second heat exchanger effluent line 90, and further heat exchanged hydrocarbon feed is extracted from second heat exchanger 25B via second heat exchanger effluent line 35. The temperature of the reaction product (i.e., the heat exchange medium) in second heat exchanger effluent line 90 may be adjusted via passage through second heater 15B prior to introduction into first heat exchanger 25A via second heater effluent line 95.

Dilution steam introduced via dilution steam feed line 40 is superheated in third heater 15C, and superheated steam extracted from third heater 15C via third heater effluent line 45 is combined in fourth heater 15D with the hydrocarbon/steam feed in second heat exchanger effluent line 35. A first stage feed stream comprising hydrocarbon and steam is extracted from fourth heater 15D via fourth heater effluent line 50.

A splitter 55A serves to split the first stage feed stream into a first portion that is introduced via first dehydrogenation reactor feed line 60A into first dehydrogenation reactor 65A, and a second or remaining portion that is introduced via second dehydrogenation reactor feed line 60B into second dehydrogenation reactor 65B, which is operated in parallel with first dehydrogenation reactor 65A. The fraction of the first stage feed stream introduced into each of the first and second dehydrogenation reactors may depend on the volumes thereof. For example, in a retrofit application in which first dehydrogenation reactor 65A and second dehydrogenation reactor 65B are of different sizes, the split ratio may be adjusted accordingly. In embodiments, approximately half of the first stage feed stream is introduced into first dehydrogenation reactor 65A, and approximately half of the first stage feed stream is introduced into second dehydrogenation reactor 65B. In embodiments, first dehydrogenation reactor 65A and second dehydrogenation reactor 65B have approximately equal volumes.

As noted hereinabove, first and second dehydrogenation reactors 65A and 65B contain therein dehydrogenation catalyst suitable for catalyzing the dehydrogenation of hydrocarbon in the first stage feed stream in the presence of steam to produce a dehydrogenation product. Dehydrogenation product and unreacted hydrocarbon are extracted from first dehydrogenation reactor 65A and second dehydrogenation reactor 65B via first reactor effluent line 70A and second reactor effluent line 70B, respectively. The product streams of first dehydrogenation reactor 65A and second dehydrogenation reactor 65B are combined in mixer 55B, providing combined first stage effluent which is extracted from mixer 55B via inter-stage or fifth heater feed line 75.

The combined first stage effluent is introduced via inter-stage or fifth heater feed line 75 into inter-stage or fifth heater 15E, which serves to heat the first stage effluent to a temperature suitable for operation of third dehydrogenation reactor 65C, thus providing a third reactor feed (also referred to herein as a second stage reactor feed) which is extracted from inter-stage heater 15E via third reactor or second stage feed line 80. Although indicated in FIG. 1 as a heater, inter-stage heater 15E may operate via any standard reheater technology, with the use of a heat exchanger shown in the embodiment of FIG. 2, and discussed further hereinbelow. In embodiments, the combined first stage effluent is heated in inter-stage or fifth heater 15E via heat exchange.

As noted hereinabove, third dehydrogenation reactor 65C contains therein dehydrogenation catalyst suitable for catalyzing the dehydrogenation of unreacted hydrocarbon in the second stage feed in the presence of steam as introduced thereto via second stage feed line 80. A second stage effluent comprising dehydrogenation product and any remaining unreacted hydrocarbon is extracted from third dehydrogenation reactor 65C via third reactor effluent line 85. As noted above, the second stage effluent extracted from third dehydrogenation reactor 65C may be compressed and subjected to product separation(s) to separate the dehydrogenation product from water and any byproducts of the reaction. In embodiments, as noted hereinabove, the second stage effluent may be subjected to heat exchange with the hydrocarbon/vaporizing steam feed, thus condensing at least a portion of the second stage effluent, prior to compression thereof and/or separation of products therefrom. For example, as discussed previously, heat may be exchanged in second heat exchanger 25B between the second stage effluent in third reactor effluent line 85 and the hydrocarbon/steam feed in first heat exchanger effluent line 30, and further heat may be exchanged in first heat exchanger 25A between the second heat exchanger effluent in second heat exchanger effluent line 90 and the hydrocarbon/steam feed in first heater effluent line 20. The temperature of the second heat exchanger effluent in second heat exchanger effluent line 90 may be adjusted via passage through second heater 15B, prior to introduction into first heat exchanger 25A via second heater effluent line 95.

Another embodiment of a dehydrogenation process according to this disclosure will now be described with reference to FIG. 2. In this embodiment, dilution feed is introduced via dilution steam feed line 40' into third heater 15C', and suitably heated steam is introduced via third heater effluent line 45' into a third heat exchanger 25C' configured to heat the combined first stage effluent in combined first stage effluent line 75 prior to introduction thereof into third dehydrogenation reactor 65C via second stage feed line 80. Heat exchanged dilution steam extracted from third heat exchanger 25C' via line 41' may be combined in fourth heater 15D with heat exchanged hydrocarbon/steam feed in second heat exchanger effluent line 35 via third heater 15C and third heater effluent line 45.

For comparison, a brief description of a conventional dehydrogenation process will now be made with reference to FIG. 3. As noted above, conventional dehydrogenation processes employ dehydrogenation reactors in series, not in parallel. Preparation of the hydrocarbon/steam feed prior to introduction into fourth heater or 'dilution steam mixing unit' 115D comprises combining vaporizing steam feed in vaporizing steam feed inlet line 105 and hydrocarbon feed in hydrocarbon feed inlet line 110 in first heater 115A, wherein the hydrocarbon is vaporized, to provide a first heater effluent comprising a vaporized hydrocarbon feed which is extracted from first heater 115A via first heater effluent line 120. Via passage through first heat exchanger 125A and second heat exchanger 125B, heat is exchanged between the vaporized hydrocarbon feed and a third reactor effluent (i.e., the product stream) in third reactor effluent line 185. In first heat exchanger 125A, heat is exchanged between the vaporized hydrocarbon feed in first heater effluent line 120 and the second heater effluent in second heater effluent line 195. Reaction product is extracted from first heat exchanger 125A via first heat exchanger effluent line 196, and heat exchanged hydrocarbon feed is extracted from first heat exchanger 125A via first heat exchanger effluent line 130. Further heat exchange of the hydrocarbon feed extracted from first heat exchanger 125A via first heat exchanger effluent line 130 is provided by introduction thereof into second heat exchanger 125B, and heat exchange with the product stream extracted from third dehydrogenation reactor 165C via third reactor effluent line 185. Reaction product is extracted from second heat exchanger 125B via second heat exchanger effluent line 190, and further heat exchanged hydrocarbon feed is extracted from second heat exchanger 125B via second heat exchanger effluent line 135. The temperature of the reaction product (i.e., the heat exchange medium) in second heat exchanger effluent line 190 may be adjusted via passage through second heater 115B prior to introduction into first heat exchanger 125A via second heater effluent line 195.

Sixth heater effluent comprising dilution steam and heat exchanged hydrocarbon/steam feed are introduced into fourth heater 115D via sixth heater effluent line 116 and second heat exchanger effluent line 135, respectively. Reactor feed is introduced into first dehydrogenation reactor 165A via fourth heater effluent line 150. The dehydrogenation product of first dehydrogenation reactor 165A extracted therefrom via first reactor effluent line 170A is heated via heat exchange with steam in fifth heater steam effluent line 129 in third heat exchanger 125C. The heat exchanged steam is extracted from third heat exchanger 125C via third heat exchanger steam effluent line 126, and the temperature thereof is raised via passage through sixth heater 115F, prior to introduction into fourth heater 115D via sixth heater effluent line 116. Increased temperature dehydrogenation product from first dehydrogenation reactor 165A is introduced as feed into second dehydrogenation reactor 165B via third heat exchanger effluent line 127.

The dehydrogenation product of second dehydrogenation reactor 165B extracted therefrom via second reactor effluent line 170B is heated via heat exchange with steam in third heater effluent line 145' in fourth heat exchanger 125D. The heat exchanged steam can be extracted from fourth heat exchanger 125D via fourth heat exchanger steam effluent line 128, and the temperature thereof is raised via passage through fifth heater 115E, prior to introduction into third heat exchanger 125C via fifth heater steam effluent line 129. Increased temperature dehydrogenation product from second dehydrogenation reactor 165B is introduced as feed into third dehydrogenation reactor 165C via third reactor feed line 180.

In the conventional process of FIG. 3, dilution steam feed in dilution steam feed line 140' is superheated in third heater 115C', and suitably heated. In the conventional process, superheated steam extracted from third heater 115C' via third heater effluent line 145' is introduced into a fourth heat exchanger 125D configured to heat the dehydrogenation product in second reactor effluent line 170B prior to introduction thereof into third dehydrogenation reactor 165C via third reactor feed line 180. As noted hereinabove, the temperature of the heat exchanged dilution steam extracted from fourth heat exchanger 125D via fourth heat exchanger steam effluent line 128 may be elevated via passage through fifth heater 115E, prior to heat exchange with dehydrogenation product of first dehydrogenation reactor 165A in third heat exchanger 125C.

As noted hereinabove, the herein-disclosed multi-stage dehydrogenation system employing a first stage containing two dehydrogenation reactors operated in parallel upstream of a second stage containing a third dehydrogenation reactor may enable a reduction in overall reactor pressure, average unit pressure advantages, an increase in desired dehydrogenation product selectivity, desirable conversion, and/or a lower energy input per pound of dehydrogenation product. For dehydrogenation processes such as the endothermic dehydrogenation of ethylbenzene to produce styrene, improved pressure conditions (i.e., a decrease in pressure) improves the selectivity. As seen in the Example below, utilizing a first stage comprising two dehydrogenation reactors operated in parallel, in series with a second stage comprising a third dehydrogenation reactor significantly reduces the differential pressure, which may improve the product selectivity. In embodiments, the total differential pressure of the herein-disclosed multi-stage dehydrogenation process is less than a total differential pressure of a conventional, otherwise similar process in which the first reactor, the second reactor, and the third reactor are connected in series, wherein the total differential pressure is measured between an inlet of the first reactor and an outlet of the third reactor. In embodiments, an overall selectivity of the herein-disclosed multi-stage dehydrogenation process is greater than an overall selectivity of a conventional, otherwise similar process in which the first reactor, the second reactor, and the third reactor are connected in series. The overall selectivity is defined as: [moles of desired product (e.g., dehydrogenation product) produced in the first reactor, the second reactor, and the third reactor]/[total moles of dehydrogenation feed species (e.g., hydrocarbon) converted in the first reactor, the second reactor, and the third reactor]. In embodiments, a total energy input of the herein-disclosed multi-stage dehydrogenation process is less than a total energy input of a conventional, otherwise similar process in which the first reactor, the second reactor, and the third reactor are connected in series.

As seen from comparing the herein-disclosed multi-stage dehydrogenation system of FIG. 1 with the conventional dehydrogenation system of FIG. 3, fifth heater 115E, sixth heater 115F, third heat exchanger 125C and fourth heat exchanger 125D are essentially replaced with inter-stage heater 15E, which may help provide the hereinabove-noted energy advantages of the herein-disclosed multi-stage dehydrogenation system and process.

The herein-disclosed multi-stage dehydrogenation system and process may run higher conversions in the first two reactors of the first stage (relative to the first two dehydrogenation reactors of a conventional dehydrogenation system wherein the first two dehydrogenation reactors are aligned in series), and more reheating may be desirable prior to introduction into the third reactor of the second stage. Furthermore, the multi-stage system and process may be particularly well suited for retrofit operations where ultra-low steam to oil (e.g., STO of about 5.5-6) and low pressure are employed.

EXAMPLE

Example 1: Comparison of Conventional and Herein-Disclosed Parallel Reactor Systems Aspen Plus simulation software was utilized to construct and compare the herein-disclosed parallel reactor system as shown in FIG. 1 with a conventional serial reactor system as shown in FIG. 3. Comparison using the reactor model of the two processes at 0.37/h ethylbenzene, 7 molar steam to oil (STO is the molar ratio of steam to hydrocarbon, e.g., ethylbenzene), and 6.5 psia outlet was performed. A 1.5 psia pressure drop was assumed for reactors at these conditions. Table 1 provides an overview of the basis for the comparison.

TABLE 1

| Basis for Process Comparison of Example 1 | | | |
|---|---|---|---|
| | Conventional | Parallel | |
| Ethylbenzene Feed | | | |
| Ethylbenzene Feed Rate to Unit | 292824 (36.9) | | lb/h (kg/s) |
| Ethylbenzene Feed Temperature | 107 (41.7) | | ° F. (° C.) |
| Ethylbenzene Feed Pressure | 39.7 (273.7) | | psia (kPa) |
| Steam Feeds | | | |
| STO | 7 | | mol/mol |
| Vaporizing Steam Feed | 74197 (9.3) | | lb/h (kg/s) |
| Vaporizing Steam Feed Temperature | 270.2 (132.3) | | ° F. (° C.) |
| Vaporizing Steam Feed Pressure | 39.7 (273.7) | | psia (kPa) |
| Dilution Steam Feed | 273623 (34.5) | | lb/h (kg/s) |
| Dilution Steam Feed Temperature | 366.5 (185.8) | | ° F. (° C.) |
| Dilution Steam Feed Pressure | 165 (1137.6) | | psia (kPa) |
| Reactor Conditions | | | |
| Reactor 1 Inlet Temperature | 1130 (610) | 1140 (615.6) | ° F. (° C.) |
| Reactor 1 Inlet Pressure | 11 (75.8) | 9.5 (62.1) | psia (kPa) |
| Reactor 1 Outlet Temperature | 1025.3 (551.8) | 993.2 (534) | ° F. (° C.) |
| Reactor 1 Outlet Pressure | 9.5 (62.1) | 8 (55.2) | psia (kPa) |
| Reactor 2 Inlet Temperature | 1145 (618.3) | 1140 (615.6) | ° F. (° C.) |
| Reactor 2 Inlet Pressure | 9.5 (62.1) | 9.5 (62.1) | psia (kPa) |
| Reactor 2 Outlet Temperature | 1065.9 (574.4) | 993.2 (534) | ° F. (° C.) |
| Reactor 2 Outlet Pressure | 8 (55.2) | 8 (55.2) | psia (kPa) |
| Reactor 3 Inlet Temperature | 1160 (626.7) | 1140 (615.6) | ° F. (° C.) |

TABLE 1-continued

Basis for Process Comparison of Example 1

|  | Conventional | Parallel | |
|---|---|---|---|
| Reactor 3 Inlet Pressure | 8 (55.2) | 8 (55.2) | psia (kPa) |
| Reactor 3 Outlet Temperature | 1097.1 (591.7) | 1043.7 (562.1) | ° F. (° C.) |
| Reactor 3 Outlet Pressure | 6.5 (44.8) | 6.5 (44.8) | psia (kPa) |
| 3-Car Garage[1] Specifications | | | |
| Reactor F/E Exch. Feed Outlet Temperature (in Line 35/135) | 965 (518.3) | | ° F. (° C.) |
| Reactor Feed Vaporizer Effluent Outlet Temperature (in Line 96/196) | 273 (133.9) | | ° F. (° C.) |

[1] 3-car garage refers to the close coupled heat exchangers 25A/125A, 15B/115B and 25B/125B in the Figures. These heat exchangers have distinct functions but are arranged such that it appears as a single unit, similar to how a garage that contains three vehicle bays appears as a single building from the outside.

The slightly elevated temperature of the ethylbenzene feed stream is the result of combining a recycle stream with fresh ethylbenzene, the vaporizing steam is from the low pressure header (25 psig), the dilution steam starts at the medium pressure header (150 psig) and the 3-car garage is operating at design start-of-run conditions for the conventional process.

The following reactions were considered for both processes:

Ethylbenzene 4 Styrene+Hydrogen       (1)

Ethylbenzene 4 Benzene+Ethylene       (2)

Ethylbenzene+Hydrogen 4 Toluene+Methane       (3)

The conversion and selectivity specifications indicated in Table 2 were utilized.

TABLE 2

Reactor Conversion and Selectivity Specifications

|  | Conventional | Parallel |
|---|---|---|
| Reactor 1 Conversion, % | 27.1 | 38 |
| Reactor 1 Selectivity to Styrene, mol % | 98.2 | 98 |
| Reactor 2 Conversion, % | 29 | 38 |
| Reactor 2 Selectivity to Styrene, mol % | 96.1 | 98 |
| Reactor 3 Conversion, % | 34.4 | 43 |
| Reactor 3 Selectivity to Styrene, mol % | 91.9 | 93 |
| Overall Conversion, % | 66 | 64.7 |
| Overall Selectivity, mol % | 95.83 | 95.94 |

The process flow for the conventional process studied is illustrated in FIG. 3; the process flow for the parallel process studied is illustrated in FIG. 1. Heat duty results for the conventional process are provided in Table 3 hereinbelow, and heat duty results for the parallel process are provided in Table 4 hereinbelow.

TABLE 3

Conventional Process Unit Operations Heat Duties

| Unit Operation | Unit Operation Description | Heat Duty, MMBTU/h (MW) |
|---|---|---|
| 115A | Vaporizer Steam Mixing | 4.47921607 (1.313) |
| 125A | Reactor Feed Vaporizer, Hot Side | −62.9435095 (−18.446) |
|  | Reactor Feed Vaporizer, Cold Side | 62.9435095 (18.446) |
|  | Reactor Feed Vaporizer, Net | 0 (0) |
| 115B | HP Steam Generator | −82.071856 (24.052) |
| 125B | Reactor Feed/Effluent Exch., Hot Side | −129.5808 (−37.974) |
|  | Reactor Feed/Effluent Exch., Cold Side | 129.5808 (37.974) |
|  | Reactor Feed/Effluent Exch., Net | 0 (0) |
| 115D | Dilution Steam Mixing | 0 (0) |
| 165A | First Dehydrogenation Reactor | 0 (0) |
| 125C | Reactor 1/Reactor 2 Reheater, Hot Side | −44.8874153 (−3.142) |
|  | Reactor 1/Reactor 2 Reheater, Cold Side | 44.8874153 (3.142) |
|  | Reactor 1/Reactor 2 Reheater, Net | 0 (0) |
| 165B | Second Dehydrogenation Reactor | 0 (0) |
| 125D | Reactor 2/Reactor 3 Reheater, Hot Side | −35.557896 (−10.420) |
|  | Reactor 2/Reactor 3 Reheater, Cold Side | 35.557896 (10.420) |
|  | Reactor 2/Reactor 3 Reheater, Net | 0 (0) |

TABLE 3-continued

Conventional Process Unit Operations Heat Duties

| Unit Operation | Unit Operation Description | Heat Duty, MMBTU/h (MW) |
|---|---|---|
| 165C | Third Dehydrogenation Reactor | 0 (0) |
| 115C' | First Steam Superheater | 151.484011 (44.393) |
| 115E | Second Steam Superheater | 34.6394569 (10.151) |
| 115F | Third Steam Superheater | 39.3110092 (11.520) |
| | Energy Totals | |
| | Energy Net Total | 147.8418372 (43.326) |
| | Energy Input Total | 229.9136932 (67.377) |
| | Energy Output Total | −82.071856 (−24.052) |
| | Energy Totals Normalized to Styrene Production | |
| | Styrene Production Rate, lb/h | 181813.893 (22.908) |
| | Energy Net Total, BTU/lb styrene (MJ/kg styrene) | 813.1492854 (1.891) |
| | Energy Input Total, BTU/lb styrene (MJ/kg styrene) | 1264.555141 (2.941) |
| | Energy Output Total, BTU/lb styrene (MJ/kg styrene) | −451.405856 (−1.050) |

TABLE 4

Parallel Process Unit Operations Heat Duties

| Unit Operation | Unit Operation Description | Heat Duty, MMBTU/h (MW) |
|---|---|---|
| 15A | Vaporizer Steam Mixing | 4.47921607 (1.313) |
| 25A | Reactor Feed Vaporizer, Hot Side | −62.9435095 (−18.446) |
| | Reactor Feed Vaporizer, Cold Side | 62.9435095 (18.446) |
| | Reactor Feed Vaporizer, Net | 0 (0) |
| 15B | HP Steam Generator | −62.028827 (18.178) |
| 25B | Reactor Feed/Effluent Exch., Hot Side | −129.5808 (−37.974) |
| | Reactor Feed/Effluent Exch., Cold Side | 129.5808 (37.974) |
| | Reactor Feed/Effluent Exch., Net | 0 (0) |
| 15C | First Steam Superheater | 148.802469 (43.607) |
| 15D | Dilution Steam Mixing | 0 (0) |
| 55A | Split Feed Stream to Reactors 1 and 2 | 0 (0) |
| 65A | First Dehydrogenation Reactor | 0 (0) |
| 65B | Second Dehydrogenation Reactor | 0 (0) |
| 55B | Recombine Reactors 1 and 2 Effluent | 0 (0) |
| 15E | Third Reactor Reheater/Inter-Stage Heater | 54.8201305 (16.065) |
| 65C | Third Dehydrogenation Reactor | 0 (0) |
| | Energy Totals | |
| | Energy Net Total | 146.0729886 (42.808) |
| | Energy Input Total | 208.1018156 (60.985) |
| | Energy Output Total | −62.028827 (18.178) |
| | Energy Totals Normalized to Styrene Production | |
| | Styrene Production Rate, lb/h (kg/s) | 178200.733 (22.453) |
| | Energy Net Total, BTU/lb styrene (MJ/kg styrene) | 819.7103688 (1.906) |
| | Energy Input Total, BTU/lb styrene (MJ/kg styrene) | 1167.794386 (2.716) |
| | Energy Output Total, BTU/lb styrene (MJ/kg styrene) | −348.0840171 (−0.810) |

Representative lab data for the standard serial mode and estimates for the parallel mode are tabulated in Table 5. The percent styrene monomer in the reactor effluent, the inlet pressure, the outlet pressure, the percent conversion, and the percent selectivity are shown for the three dehydrogenation reactors of the standard serial mode and the parallel mode.

TABLE 5

Summary of Data from Serial and Parallel Reactor Systems

|  | Serial Mode | | | Parallel Mode for Reactors 65A/65B | | |
| --- | --- | --- | --- | --- | --- | --- |
|  | 165A | 165B | 165C | 65A | 65B | 65C |
| Styrene Monomer, % | 27.1 | 47.1 | 63.5 | 37 | 37 | 64 |
| Inlet Pressure, psia (kPa) | 11 (75.8) | 9.5 (62.1) | 8 (55.2) | 9.5 (62.1) | 9.5 (62.1) | 8 (55.2) |
| Outlet Pressure, psia (kPa) | 9.5 (62.1) | 8 (55.2) | 6.5 (44.8) | 8 (55.2) | 8 (55.2) | 6.5 (44.8) |
| Conversion, % | 27.1 | 29 | 34.4 | 38 | 38 | 43 |
| Selectivity, % | 98.2 | 96.1 | 91.9 | 98 | 98 | 93 |

As indicated in Tables 3 and 4, the net energy for the conventional process is slightly lower than for the parallel process. However, this can be attributed to the high pressure steam that is generated. The parallel process actually requires less energy input per pound of styrene. Additionally the process is able to operate at lower overall pressure and higher selectivity as specified. The parallel reactor process thus demonstrates advantages in energy input, average unit pressure, total differential pressure, and overall selectivity for the conditions modeled.

Additional Description

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: A multi-stage dehydrogenation process comprising: contacting, in a first stage, a feed stream comprising a hydrocarbon and steam with a dehydrogenation catalyst under dehydrogenation conditions to yield a first stage effluent; heating the first stage effluent; and contacting, in a second stage, the heated first stage effluent with a dehydrogenation catalyst under dehydrogenation conditions to yield a second stage effluent comprising a dehydrogenation product, wherein the first stage includes a first reactor and a second reactor arranged in parallel, and wherein the second stage includes a third reactor connected in series with the first reactor and the second reactor.

B: A multi-stage dehydrogenation system comprising: a feed stream comprising a hydrocarbon and steam; a first stage having a first reactor and a second reactor arranged in parallel, wherein the first reactor contains a dehydrogenation catalyst and has a first reactor inlet which receives a portion of the feed stream, wherein the second reactor contains a dehydration catalyst and has a second reactor inlet which receives a remaining portion of the feed stream, and wherein the first stage is effective to convert at least a portion of the hydrocarbon to a dehydrogenation product by contacting the hydrocarbon with the dehydrogenation catalyst in the first and second reactors under dehydrogenation conditions; an inter-stage heater fluidly connected to a first reactor outlet of the first reactor and receiving a first reactor effluent and fluidly connected to a second reactor outlet of the second reactor and receiving a second reactor effluent; a second stage having a third reactor, wherein the third reactor contains a dehydrogenation catalyst and has a third reactor inlet in fluid communication with the inter-stage heater, and wherein the second stage is effective to convert unreacted hydrocarbon received from the inter-stage heater to the dehydrogenation product by contacting the unreacted hydrocarbon with the dehydrogenation catalyst in the third reactor under dehydrogenation conditions to provide a second stage effluent comprising a third reactor effluent.

C: A multi-stage dehydrogenation process comprising: combining steam and ethylbenzene to form a feed stream; heating the feed stream to yield a heated feed stream; splitting the heated feed stream into a first portion and a second portion; feeding the first portion of the feed stream to a first reactor containing a dehydrogenation catalyst, wherein ethylbenzene is converted to styrene; feeding the second portion of the feed stream to a second reactor containing a dehydrogenation catalyst, wherein ethylbenzene is converted to styrene; recovering from the first reactor a first effluent comprising unreacted ethylbenzene and styrene; recovering from the second reactor a second effluent comprising unreacted ethylbenzene and styrene; combining the first effluent and the second effluent into a combined effluent; heating the combined effluent to yield a heated combined effluent; feeding the heated combined effluent to a third reactor containing a dehydrogenation catalyst, wherein at least a portion of the unreacted ethylbenzene present in the heated combined effluent is converted to styrene; and recovering from the third reactor a third effluent comprising unreacted ethylbenzene and styrene.

Each of embodiments A, B and C may have one or more of the following additional elements: Element 1: wherein contacting the feed stream in the first stage comprises: contacting a first portion of the feed stream with the dehydrogenation catalyst in the first reactor to yield a first reactor effluent; and contacting a second portion of the feed stream with the dehydrogenation catalyst in the second reactor to yield a second reactor effluent. Element 2: further comprising: combining the first reactor effluent and the second reactor effluent to form the first stage effluent prior to the step of heating. Element 3: further comprising: heat exchanging the feed stream with the second stage effluent, thereby condensing a portion of the second stage effluent; compressing the second stage effluent after the step of heat exchanging; and separating the dehydrogenation product from the second stage effluent. Element 4: wherein a total differential pressure of the multi-stage dehydrogenation process is less than a total differential pressure of an otherwise similar process in which the first reactor, the second reactor, and the third reactor are connected in series, wherein the total differential pressure is measured between an inlet of the first reactor and an outlet of the third reactor. Element 5: wherein an overall selectivity of the multi-stage dehydrogenation process is greater than an overall selectivity of an otherwise similar process in which the first reactor, the second reactor, and the third reactor are connected in series, wherein the overall selectivity is defined as: [moles of dehydrogenation product produced in the first reactor, the second reactor, and the third reactor]/[total moles of hydrocarbon converted in the first reactor, the second reactor, and the third reactor]. Element 6: wherein a total energy input of the multi-stage dehydrogenation process is less than a total energy input of an otherwise similar process in which the first reactor, the second reactor, and the third reactor are connected in series. Element 7: wherein the hydrocarbon is ethylbenzene, and wherein the dehydrogenation product comprises styrene. Element 8: wherein each of the first reactor, the second reactor, and the third reactor is an adiabatic reactor. Element 9: wherein heating the first stage effluent uses a heat exchanger. Element 10: wherein the first reactor effluent and the second reactor effluent are combined to form a first stage effluent which feeds to the inter-stage heater. Element 11: wherein the inter-stage heater is a heat exchanger which uses steam as a heating fluid. Element 12: further comprising: a first heat exchanger which exchanges a first heat between the second stage effluent and the feed stream; and a second heat exchanger which exchanges a second heat between the second stage effluent and the feed stream. Element 13: further comprising: a compressor downstream of the first heat exchanger and the second heat exchanger and configured to compress the second stage effluent; and a separation system downstream of the compressor and configured to separate a dehydrogenation product from the second stage effluent. Element 14: wherein a total differential pressure of the multi-stage dehydrogenation system is less than a total differential pressure of an otherwise similar system in which the first reactor, the second reactor, and the third reactor are connected in series, wherein the total differential pressure is measured between the first reactor inlet and an outlet of the third reactor. Element 15: wherein an overall selectivity of the multi-stage dehydrogenation system is greater than an overall selectivity of an otherwise similar system in which the first reactor, the second reactor, and the third reactor are connected in series, wherein the overall selectivity is defined as: [moles of dehydrogenation product produced in the first reactor, the second reactor, and the third reactor]/[total moles of hydrocarbon converted in the first reactor, the second reactor, and the third reactor]. Element 16: wherein a total energy input of the multi-stage dehydrogenation system is less than a total energy input of an otherwise similar system in which the first reactor, the second reactor, and the third reactor are connected in series. Element 17: wherein the hydrocarbon is ethylbenzene, and wherein the dehydrogenation product comprises styrene. Element 18: wherein each of the first reactor, the second reactor, and the third reactor is an adiabatic reactor.

While preferred embodiments of the invention have been shown and described, modifications thereof can be made by one skilled in the art without departing from the teachings of this disclosure. The embodiments described herein are exemplary only, and are not intended to be limiting. Many variations and modifications of the invention disclosed herein are possible and are within the scope of the invention.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A multi-stage dehydrogenation process comprising:
   contacting, in a first stage consisting of a first reactor and a second reactor arranged in parallel, a feed stream comprising a hydrocarbon and steam with a dehydrogenation catalyst under dehydrogenation conditions to yield a first stage effluent, wherein the contacting comprises splitting the feed stream into a first portion and a second portion, feeding the first portion of the feed stream to the first reactor and feeding the second portion to the second reactor, and wherein the first reactor and the second reactor are separate vessels and do not share a common housing;
   combining a first reactor effluent from the first reactor with a second reactor effluent from the second reactor in a mixer disposed between the first stage and the second stage, to form a first stage effluent, wherein the mixer does not share a common housing with the first reactor or the second reactor;
   heating the first stage effluent to form a heated first stage effluent;
   contacting in a second stage comprising a third reactor connected in series with the reactors in the first stage, the heated first stage effluent with a dehydrogenation catalyst under dehydrogenation conditions to yield a second stage effluent comprising a dehydrogenation product,
wherein an overall selectivity of the multi-stage dehydrogenation process is increased relative to an overall selectivity of an otherwise similar process in which the first reactor, the second reactor, and the third reactor are connected in series, wherein the overall selectivity is defined as: [moles of dehydrogenation product produced in the first reactor, the second reactor, and the third reactor]/[total moles of hydrocarbon converted in the first reactor, the second reactor, and the third reactor];
heat exchanging the feed stream with the second stage effluent, thereby condensing a portion of the second stage effluent;
compressing the second stage effluent after the step of heat exchanging; and
separating the dehydrogenation product from the second stage effluent.

2. The process of claim 1, wherein the contacting the feed stream in the first stage comprises:
contacting the first portion of the feed stream with the dehydrogenation catalyst in the first reactor to yield the first reactor effluent; and
contacting the second portion of the feed stream with the dehydrogenation catalyst in the second reactor to yield the second reactor effluent.

3. The process of claim 1, wherein a total differential pressure of the multi-stage dehydrogenation process is less than a total differential pressure of an otherwise similar process in which the first reactor, the second reactor, and the third reactor are connected in series, wherein the total differential pressure is measured between an inlet of the first reactor and an outlet of the third reactor.

4. The process of claim 1, wherein an overall selectivity of the multi-stage dehydrogenation process is greater than an overall selectivity of an otherwise similar process in which the first reactor, the second reactor, and the third reactor are connected in series, wherein the overall selectivity is defined as:

[moles of dehydrogenation product produced in the first reactor, the second reactor, and the third reactor]/[total moles of hydrocarbon converted in the first reactor, the second reactor, and the third reactor].

5. The process of claim 1, wherein a total energy input of the multi-stage dehydrogenation process is less than a total energy input of an otherwise similar process in which the first reactor, the second reactor, and the third reactor are connected in series.

6. The process of claim 1, wherein the hydrocarbon is ethylbenzene, and wherein the dehydrogenation product comprises styrene.

7. The process of claim 1, wherein each of the first reactor, the second reactor, and the third reactor is an adiabatic reactor.

8. The process of claim 1, wherein the heating the first stage effluent uses a heat exchanger.

9. A multi-stage dehydrogenation process comprising:
combining steam and ethylbenzene to form a feed stream;
heating the feed stream to yield a heated feed stream;
splitting the heated feed stream into a first portion and a second portion;
feeding the first portion of the heated feed stream to a first reactor of a first stage and feeding the second portion of the heated feed stream to a second reactor of the first stage, wherein the first stage consisting of the first reactor and the second reactor, wherein the first reactor and the second reactor contain a dehydrogenation catalyst, wherein ethylbenzene is converted to styrene in the first reactor and the second reactor, and wherein the first reactor and the second reactor are separate vessels and do not share a common housing;
recovering from the first reactor a first effluent comprising unreacted ethylbenzene and styrene;
recovering from the second reactor a second effluent comprising unreacted ethylbenzene and styrene;
combining the first effluent and the second effluent into a combined effluent in a mixer, wherein the mixer is located downstream of the first reactor and the second reactor, but upstream of a second stage;
heating the combined effluent to yield a heated combined effluent;
feeding the heated combined effluent to the second stage comprising a third reactor containing a dehydrogenation catalyst to yield a second stage effluent, wherein at least a portion of the unreacted ethylbenzene present in the heated combined effluent is converted to styrene; and
recovering from the third reactor the second stage effluent comprising unreacted ethylbenzene and styrene,
wherein an overall selectivity of the multi-stage dehydrogenation process is increased relative to an overall selectivity of an otherwise similar process in which the first reactor, the second reactor, and the third reactor are connected in series, wherein the overall selectivity is defined as: [moles of dehydrogenation product produced in the first reactor, the second reactor, and the third reactor]/[total moles of hydrocarbon converted in the first reactor, the second reactor, and the third reactor], and
wherein heating the feed stream comprises heating the feed stream to a dehydrogenation temperature by exchanging a first heat between the second stage effluent and the feed stream via a first heat exchanger, and exchanging a second heat between the second stage effluent and the feed stream via a second heat exchanger.

10. The process of claim 9, wherein a first stage feed consists of the heated feed stream, and wherein the splitting comprises splitting the heated feed stream into portions consisting of the first portion and the second portion.

11. The process of claim 9, wherein a fraction of the first stage feed introduced into the first reactor via the first portion and a fraction of the first stage feed introduced into the second reactor via the second portion is based on a volume of the first reactor and a volume of the second reactor.

12. The process of claim 1, wherein the process further comprises splitting the feed stream contacted with the dehydrogenation catalyst in the first stage into portions consisting of a first portion and a remaining portion, and wherein the contacting, in the first stage, the feed stream comprising the hydrocarbon and steam with the dehydrogenation catalyst under dehydrogenation conditions to yield the first stage effluent further comprises introducing the first portion of the feed stream into the first reactor and introducing the remaining portion of the feed stream into the second reactor.

13. The process of claim 12, wherein a fraction of the feed stream introduced into the first reactor via the first portion and a fraction of the feed stream introduced into the second reactor via the second portion is based on a volume of the first reactor and a volume of the second reactor.

14. The process of claim 1, further comprising heating the feed stream comprising the hydrocarbon and steam to a dehydrogenation temperature prior to contacting the feed stream with the dehydrogenation catalyst in the first stage.

15. The process of claim 14, wherein the heating the feed stream to the dehydrogenation temperature comprises exchanging a first heat between the second stage effluent and the feed stream via a first heat exchanger, and exchanging a second heat between the second stage effluent and the feed stream via a second heat exchanger.

16. The process of claim 15, wherein the process further comprises heating the second stage effluent between the first heat exchanger and the second heat exchanger.

17. The process of claim 1, wherein the process further comprises forming the feed stream by introducing vaporizing steam and the hydrocarbon into a vaporizing steam mixing unit comprising a heater operable to vaporize the hydrocarbon introduced thereto.

18. The process of claim 9, wherein the process further comprises heating the second stage effluent between the first heat exchanger and the second heat exchanger.

\* \* \* \* \*